(12) United States Patent
Tsuchiya et al.

(10) Patent No.: US 11,141,167 B2
(45) Date of Patent: Oct. 12, 2021

(54) CLIP TREATMENT TOOL

(71) Applicant: FUJIFILM Corporation, Tokyo (JP)

(72) Inventors: Syuji Tsuchiya, Kanagawa (JP); Koji Itoh, Kanagawa (JP); Issei Suzuki, Kanagawa (JP)

(73) Assignee: FUJIFILM Corporation, Tokyo (JP)

( * ) Notice: Subject to any disclaimer, the term of this patent is extended or adjusted under 35 U.S.C. 154(b) by 173 days.

(21) Appl. No.: 16/712,929

(22) Filed: Dec. 12, 2019

(65) Prior Publication Data

US 2020/0113572 A1 Apr. 16, 2020

Related U.S. Application Data

(63) Continuation of application No. PCT/JP2018/015150, filed on Apr. 11, 2018.

(30) Foreign Application Priority Data

Jun. 21, 2017 (JP) .............................. JP2017-121530

(51) Int. Cl.
*A61B 17/128* (2006.01)
*A61B 17/00* (2006.01)

(52) U.S. Cl.
CPC .. *A61B 17/1285* (2013.01); *A61B 2017/0046* (2013.01); *A61B 2017/00477* (2013.01)

(58) Field of Classification Search
CPC ....... A61B 17/08; A61B 17/083; A61B 17/10; A61B 17/122; A61B 17/128; A61B 17/1285

See application file for complete search history.

(56) References Cited

U.S. PATENT DOCUMENTS 5,766,189 A 6/1998 Matsuno
6,991,634 B2 * 1/2006 Sugiyama ............ A61B 17/122
606/142
(Continued)

FOREIGN PATENT DOCUMENTS

EP 3603541 2/2020
JP H026011 1/1990
(Continued)

OTHER PUBLICATIONS

"Search Report of Europe Counterpart Application", dated Mar. 30, 2020, p. 1-p. 7.
(Continued)

*Primary Examiner* — Ryan J. Severson
(74) *Attorney, Agent, or Firm* — JCIPRNET (57) ABSTRACT

A clip treatment tool includes a clip body that has two arm portions and a folded portion, the folded portion connecting proximal end parts of the two arm portions; a pressing tube that allows the clip body to be contained therein in accordance with movement of the clip body from a distal end side toward a proximal end side; a coupling member that couples the clip body and an operation wire to each other; and an urging member that urges the coupling member relative to the pressing tube from the proximal end side toward the distal end side. The pressing tube has a latched portion, and the coupling member has a latch portion. In accordance with movement of the operation wire from the distal end side toward the proximal end side, the latch portion is latched to the latched portion, and the coupling member is locked to the pressing tube.

10 Claims, 5 Drawing Sheets

(56) References Cited

U.S. PATENT DOCUMENTS

| | | |
|---|---|---|
| 7,452,327 B2 | 11/2008 | Durgin et al. |
| 8,083,668 B2 | 12/2011 | Durgin et al. |
| 8,157,824 B2 * | 4/2012 | Kimura ............... A61B 17/1222 606/157 |
| 8,974,371 B2 | 3/2015 | Durgin et al. |
| 9,339,270 B2 | 5/2016 | Martinez et al. |
| 9,370,371 B2 | 6/2016 | Durgin et al. |
| 9,510,836 B2 * | 12/2016 | Zhu ...................... A61B 17/122 |
| 9,795,390 B2 * | 10/2017 | Jin ...................... A61B 17/1285 |
| 9,980,725 B2 | 5/2018 | Durgin et al. |
| 2002/0177861 A1 | 11/2002 | Sugiyama et al. |
| 2014/0171973 A1 | 6/2014 | Zhu |
| 2015/0230799 A1 | 8/2015 | Satake et al. |
| 2016/0367258 A1 | 12/2016 | Jin et al. |
| 2018/0235608 A1 | 8/2018 | Durgin et al. |
| 2020/0113572 A1 * | 4/2020 | Tsuchiya ............... A61B 17/122 |

FOREIGN PATENT DOCUMENTS

| | | |
|---|---|---|
| JP | H09289989 | 11/1997 |
| JP | 2008289524 | 12/2008 |
| JP | 4921173 | 4/2012 |
| JP | 2013544128 | 12/2013 |
| JP | 5750619 | 7/2015 |
| KR | 101201083 | 11/2012 |

OTHER PUBLICATIONS

Office Action of Japan Counterpart Application, with English translation thereof, dated Oct. 13, 2020, pp. 1-8.

"International Search Report (Form PCT/ISA/210) of PCT/JP2018/015150," dated Jun. 26, 2018, with English translation thereof, pp. 1-5.

"International Search Report (Form PCT/ISA/237) of PCT/JP2018/015150," dated Jun. 26, 2018, with English translation thereof, pp. 1-12.

* cited by examiner

CLIP TREATMENT TOOL

CROSS-REFERENCE TO RELATED APPLICATIONS

This application is a Continuation of PCT International Application No. PCT/JP2018/015150 filed on Apr. 11, 2018, which claims priority under 35 U.S.C § 119(a) to Japanese Patent Application No. 2017-121530 filed on Jun. 21, 2017. Each of the above application(s) is hereby expressly incorporated by reference, in its entirety, into the present application.

BACKGROUND OF THE INVENTION

The present invention relates to a clip treatment tool for an endoscope, which is used, for example, to close a wound and to stop bleeding in a living body.

2. Description of the Related Art

A clip treatment tool for an endoscope is used, for example, to close a wound and to stop bleeding by extruding arm portions of a clip from a distal end of the endoscope, which is inserted into a living body, and by ligating a treatment part, such as the wound and the bleeding part, with distal end parts of the arm portions of the clip.

Examples of such a clip treatment tool known to date include clip treatment tools that can freely open and close arm portions of a clip, as described in JP5750619B, JP4921173B, U.S. Pat. No. 9,339,270B, US2016/0367258A, and JP2008-289524A. By using the known technologies described in these patent documents, for example, it is possible to freely open and close arm portions of a clip in the body of a patient to hold a treatment part over again, and therefore it is possible to apply the clip to an accurate position on the treatment part and to perform treatment such as stoppage of bleeding.

SUMMARY OF THE INVENTION

However, once the treatment part has been ligated by the clip, the clip is placed in the body of the patient. Therefore, when the clip is placed in the body at a position displaced from a target position to be ligated due to an erroneous operation or the like, and when, for example, the clip placed in the body becomes unnecessary after bleeding or the like has been sufficiently stopped, the clip remains placed in the living body, and it is necessary to wait until the clip is naturally removed due to a change in body tissue of the patient. That is, there is a problem in that it is not possible to remove the clip at a desirable timing.

An object of the present invention is to provide a clip treatment tool with which, after the clip has been once applied, it is possible to reliably maintain the applied state, and it is possible to remove a clip placed in a living body at any desirable timing.

In order to achieve the object, the present invention provides a clip treatment tool including: a clip body that has two arm portions that face each other and open and close and a folded portion that connects proximal end parts of the two arm portions; a pressing tube that opens the two arm portions and exposes the clip body in accordance with movement of the clip body from a proximal end side toward a distal end side and that closes the two arm portions and allows the clip body to be contained therein in accordance with movement of the clip body from the distal end side toward the proximal end side; a coupling member that has a distal end part engaged with the folded portion of the clip body and a proximal end part to which a distal end part of an operation wire is removably latched, the coupling member coupling the clip body and the operation wire to each other; and an urging member that is contained in the pressing tube and that urges the coupling member relative to the pressing tube from the proximal end side toward the distal end side. The pressing tube has a latched portion disposed on the proximal end side of the pressing tube, and the coupling member has a latch portion disposed on the proximal end side of the coupling member. In accordance with movement of the operation wire from the distal end side toward the proximal end side, the coupling member moves from the distal end side toward the proximal end side, the latch portion is latched to the latched portion, and the coupling member is locked to the pressing tube.

Preferably, in accordance with movement of the coupling member from the distal end side toward the proximal end side, the two arm portions are pressed by a distal end part of the pressing tube in directions toward each other and elastically deform, and the two arm portions gradually close from an open state and enter a closed state.

Preferably, the latch portion has two top portions that are formed so that end parts thereof on the distal end side are angular parts and two inclined portions that are respectively disposed on the proximal end side from the two top portions, and the two top portions and the two inclined portions extend so as to face each other; the latched portion has a proximal end surface formed on the proximal end side of the pressing tube, and a latch hole is formed in the proximal end surface of the pressing tube, the latch hole having an inside diameter that is smaller than an outside diameter of the two top portions at the angular parts on the distal end side; and, in accordance with movement of the coupling member from the distal end side toward the proximal end side, the two inclined portions are pressed by a distal end part of the latch hole in directions toward each other and pass through the latch hole, the angular parts of the two top portions move to positions beyond the latch hole of the latched portion, the two top portions move away from each other due to an elastic force and the angular parts of the two top portions are latched to the proximal end surface of the latched portion, and the coupling member is locked to the pressing tube while the two arm portions are in the closed state.

Preferably, the coupling member has a containing portion that is formed in the coupling member on the distal end side relative to the two top portions, and the operation wire has a wire stopper that is disposed on the distal end side of the operation wire and that is contained in the containing portion; and, in a state in which the coupling member is locked to the pressing tube, in accordance with movement of the operation wire from the distal end side toward the proximal end side, the two top portions are pushed and expanded by an end part of the wire stopper on the proximal end side and move away from each other, the wire stopper is removed from the containing portion, and the coupling member and the operation wire are separated from each other.

Preferably, in a state in which the coupling member and the operation wire are separated from each other, the two top portions are pressed from both outer sides, the outside diameter of the two top portions at the angular parts on the distal end side becomes smaller than the inside diameter of the latch hole, the coupling member is urged by the urging member and moves from the proximal end side toward the distal end side, and, in accordance with movement of the coupling member from the proximal end side toward the distal end side, the clip body moves from the proximal end side toward the distal end side, and the two arm portions gradually open from the closed state and return to the open state.

Preferably, the pressing tube has a constricted portion in a middle part thereof in an axial direction, the constricted portion having an inside diameter smaller than an inside diameter at both end parts of the pressing tube, and the coupling member has a protruding portion on the distal end side, the protruding portion having an outside diameter that is larger than an outside diameter at a middle part of the coupling member; and the urging member is disposed between the protruding portion and the constricted portion, and the latch portion is movable on the proximal end side relative to the constricted portion.

With the present invention, until a treatment part is ligated by a clip unit, which is composed of the pressing tube, the coupling member, and the urging member, it is possible to hold the treatment part over again by using the two arm portions; and, after the treatment part has been ligated by the clip unit, because the coupling member and the pressing tube are locked, it is possible to reliably maintain the state in which the treatment part is ligated by the clip unit. Moreover, after the clip unit is placed at the treatment part, it is possible to remove the clip unit from the treatment part by unlocking the coupling member and the pressing tube at any desirable timing.

DESCRIPTION OF THE PREFERRED EMBODIMENTS

Hereafter, a clip treatment tool according to the present invention will be described in detail based on preferred embodiments illustrated in the drawings.

Figure 1:
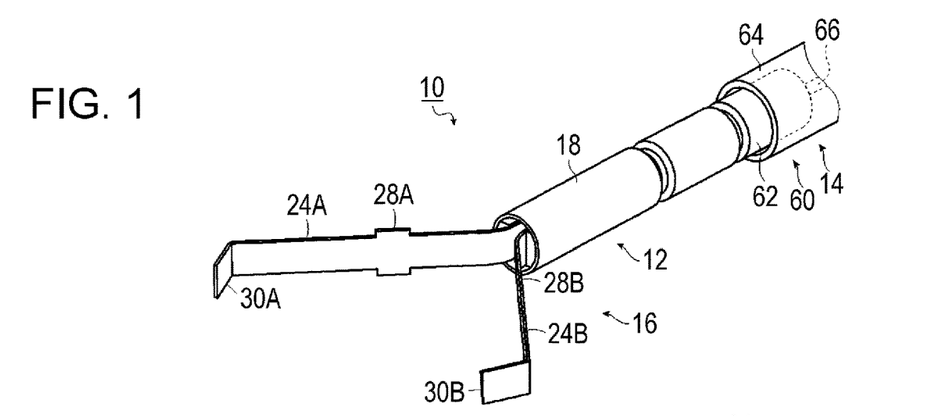
FIG. 1 is a partially see-through external perspective view of a clip treatment tool according to an embodiment of the present invention.
Figure 2:
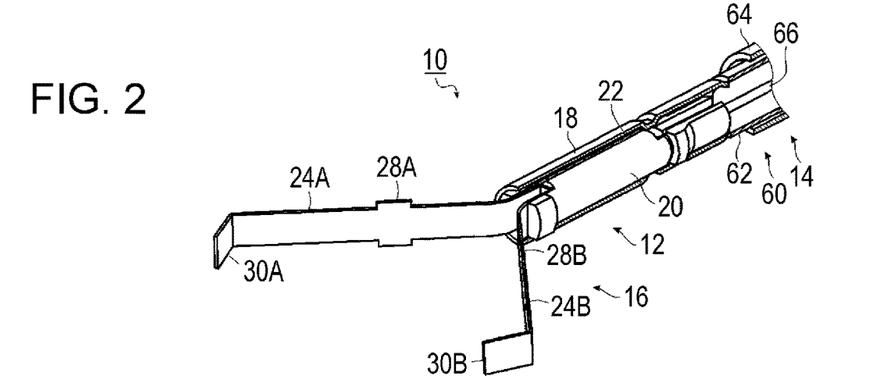
FIG. 2 is a partial cut-away perspective view of the clip treatment tool illustrated in FIG. 1.

FIG. 1 is a partially see-through external perspective view of a clip treatment tool according to an embodiment of the present invention. FIG. 2 is a partially cut-away perspective view of the clip treatment tool illustrated in FIG. 1.

Figure 9A:
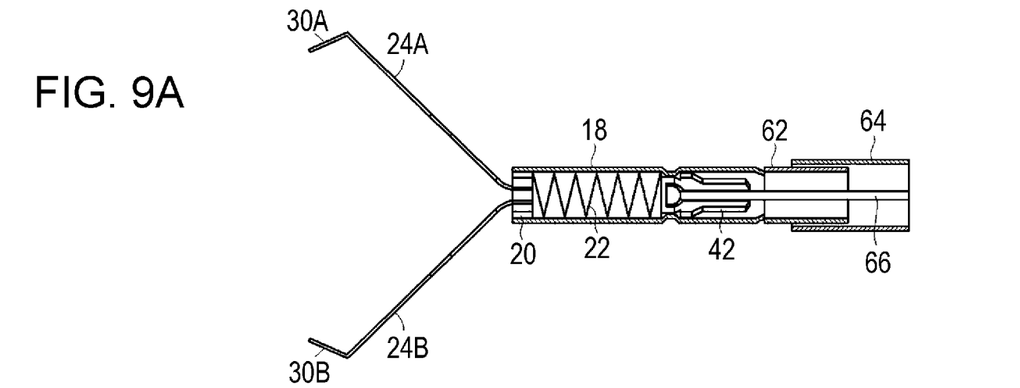
FIG. 9A is a partially see-through external side view of the clip treatment tool according to the embodiment of the present invention, in a state in which two arm portions of the clip body are in an open state.

In the present embodiment, a first direction is defined as the direction in which two clip pieces face each other (direction perpendicular to the plane of FIG. 9B), and a second direction is defined as the direction perpendicular to both of the first direction and the axial direction of a pressing tube (direction perpendicular to the plane of FIG. 9A). In the clip treatment tool, a side on which a treatment part is located is defined as the distal end side, and a side on which an operator is located is defined as the proximal end side.

In all figures, in order to facilitate understanding, the dimensions, such as the thickness and the length, of each element of the present embodiment are appropriately changed from the actual dimensions, as necessary.

A clip treatment tool 10 illustrated in FIGS. 1 and 2 includes a clip unit 12 and a treatment tool body 14. When operated by an operator, for example, the clip treatment tool 10 is inserted from a treatment tool inlet of an operation portion of an endoscope, is extruded from a treatment tool outlet of a distal end surface of an insertion portion of the endoscope that has been inserted into the body of a patient, and ligates a treatment part by using the clip unit 12.

The clip unit 12 includes a clip body 16, a pressing tube 18, a coupling member 20, and an urging member 22.

Figure 3:
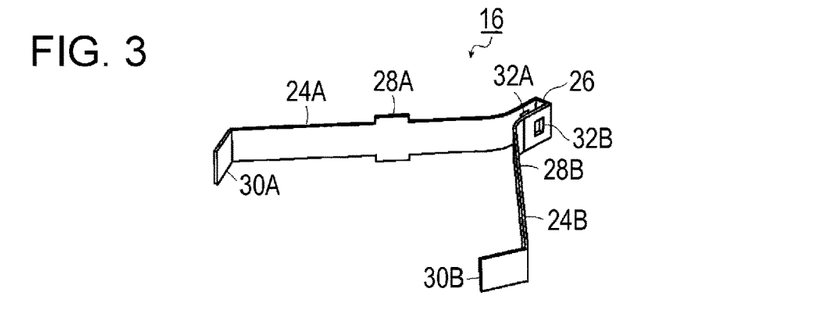
FIG. 3 is an external perspective view of a clip body according to the embodiment.

FIG. 3 is an external perspective view of the clip body according to the embodiment.

As illustrated in FIG. 3, the clip body 16 has two arm portions, which are a first arm portion 24A and a second arm portion 24B, that face each other and that open and close, and a folded portion 26 that connects proximal end parts of the two arm portions 24A and 24B.

The two arm portions 24A and 24B and the folded portion 26 are integrally formed by being bent respectively at a position between the first arm portion 24A and the folded portion 26 and a position between the second arm portion 24B and the folded portion 26. The folded portion 26 has a substantial C-shape, as seen in the second direction. The two arm portions 24A and 24B face each other, and, in a state in which an external force is not applied, extend so as to become farther from each other from the proximal end side toward the distal end side.

The first arm portion 24A has a first protruding portion 28A and a first claw portion 30A.

The first protruding portion 28A is a portion that restricts movement of the clip body 16 from the distal end side toward the proximal end side. The first protruding portion 28A is formed at a middle part of the first arm portion 24A in the extension direction so as to protrude from both end parts of the first arm portion 24A in the width direction (the second direction). That is, the size of the first protruding portion 28A in the width direction is larger than the size of the other parts of the first arm portion 24A in the width direction.

The first claw portion 30A is formed at a distal end part of the first arm portion 24A. The first claw portion 30A is formed by bending the distal end part of the first arm portion 24A by a constant angle in a direction toward the second arm portion 24B.

The second arm portion 24B is configured similarly to the first arm portion 24A. The second arm portion 24B has a second protruding portion 28B and a second claw portion 30B, which are formed at positions respectively corresponding to the first protruding portion 28A and the first claw portion 30A of the first arm portion 24A. The first claw portion 30A and the second claw portion 30B are portions for holding a treatment part therebetween and ligating the treatment part.

At middle parts of both side surfaces of the folded portion 26 in the first direction, rectangular engagement holes 32A and 32B, which are engageable with the coupling member 20, are respectively formed.

Figure 4:
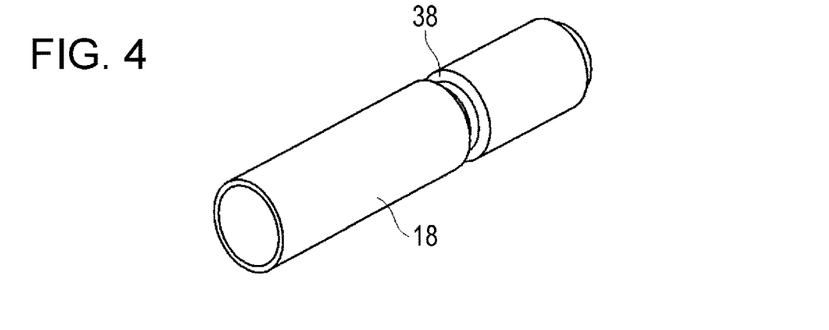
FIG. 4 is an external perspective view of a pressing tube according to the embodiment.

FIG. 4 is an external perspective view of the pressing tube according to the embodiment.

As illustrated in FIG. 4, the pressing tube 18 has a latched portion 34 (see FIG. 6) on the proximal end side. The latched portion 34 is a portion to which a latch portion 42 of the coupling member 20 is latched, and is formed by reducing the diameter of the proximal end side of the pressing tube 18. In other words, the latched portion 34 has a proximal end surface that is formed on the proximal end side of the pressing tube 18, and a latch hole 36 (see FIG. 6) is formed in the proximal end surface of the pressing tube 18.

The pressing tube 18 has a constricted portion 38, whose inside diameter is smaller than the inside diameter at both end parts, at a middle part in the axial direction.

The pressing tube 18 opens the two arm portions 24A and 24B and exposes the clip body 16 in accordance with movement of the clip body 16 from the proximal end side toward the distal end side, and closes the two arm portions 24A and 24B and allows the clip body 16 to be contained therein in accordance with movement of the clip body 16 from the distal end side toward the proximal end side.

To be more specific, in accordance with movement of the clip body 16 from the distal end side toward the proximal end side, the two arm portions 24A and 24B are pressed by a distal end part of the pressing tube 18 in directions toward each other and elastically deform, and the two arm portions 24A and 24B gradually close from an open state and finally enter a closed state. On the other hand, in accordance with movement of the clip body 16 from the proximal end side toward the distal end side, the two arm portions 24A and 24B gradually open from the closed state due to an elastic force and finally enter the open state.

Figure 5:
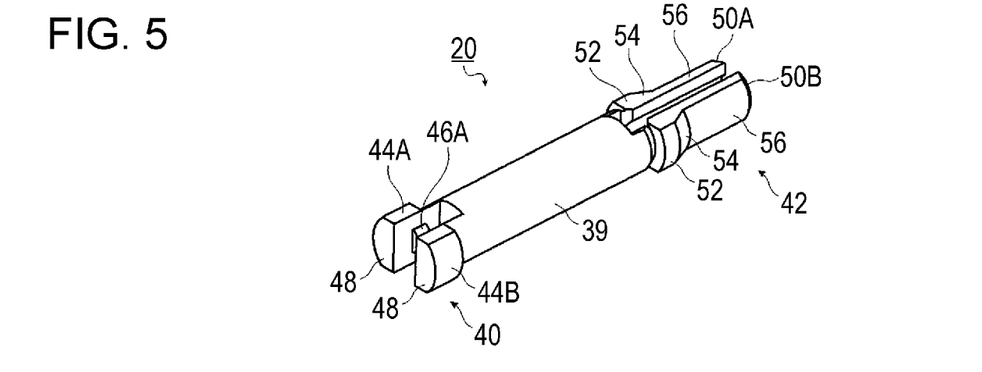
FIG. 5 is an external perspective view of a coupling member according to the embodiment.

FIG. 5 is an external perspective view of the coupling member according to the embodiment.

As illustrated in FIG. 5, the coupling member 20 has a coupling member body 39, an engagement portion 40 disposed on the distal end side of the coupling member body 39, and the latch portion 42 disposed on the proximal end side of the coupling member body 39. For example, the coupling member 20 is made of a biocompatible resin. The coupling member 20 is contained in the pressing tube 18 when the two arm portions 24A and 24B are in the open state.

The coupling member body 39 has a cylindrical shape, and has an outside diameter larger than the inside diameter of the constricted portion 38 of the pressing tube 18.

The engagement portion 40 is a portion that serves a distal end part that is engaged with the folded portion 26 of the clip body 16, and is disposed on the distal end side from the coupling member body 39. The coupling member body 39 and the engagement portion 40 are integrally formed. The engagement portion 40 has a first engagement member 44A and a second engagement member 44B. The first engagement member 44A and the second engagement member 44B extend parallelly from a distal end part of the coupling member body 39 toward the distal end side so as to face each other. The first engagement member 44A and the second engagement member 44B are disposed with a constant distance therebetween in the first direction. The distance between the first engagement member 44A and the second engagement member 44B is slightly larger than the size of the folded portion 26 of the clip body 16 in the first direction.

The first engagement member 44A has a first projecting portion 46A, which protrudes from the first engagement member 44A toward the second engagement member 44B, on an inner surface thereof facing the second engagement member 44B. Likewise, the second engagement member 44B has a second projecting portion (not shown), which protrudes from the second engagement member 44B toward the first engagement member 44A, on an inner surface thereof facing the first engagement member 44A. The shape of each of the first projecting portion 46A and the second projecting portion as seen in the first direction is a rectangular shape, which is similar to the shape of each of the engagement holes 32A and 32B of the clip body 16 as seen in the first direction. The outside dimensions of each of the first projecting portion 46A and the second projecting portion is slightly smaller than the inside dimensions of each of the engagement holes 32A and 32B.

The first engagement member 44A and the second engagement member 44B are disposed so as to clamp the folded portion 26 of the clip body 16 from both outer sides in the first direction, and the first projecting portion 46A and the second projecting portion are respectively inserted into the engagement holes 32A and 32B of the folded portion 26. Thus, the folded portion 26 and the engagement portion 40 are engaged with each other, and the clip body 16 and the coupling member 20 are engaged with each other.

Moreover, the coupling member 20 has protruding portions 48 on the distal end side. The outside diameter of the protruding portions 48 is larger than the outside diameter of a middle part of the coupling member 20, that is, the coupling member body 39, and is smaller than the inside diameter of the pressing tube 18. In the present embodiment, the protruding portions 48 are respectively formed on the outer surfaces of the first engagement member 44A and the second engagement member 44B on the distal end side. That is, the protruding portions 48 of the first engagement member 44A and the second engagement member 44B have proximal end surfaces whose end parts on the proximal end side are angular parts.

The latch portion 42 is disposed on the proximal end side from the coupling member body 39, and is integrally formed with the coupling member body 39. The latch portion 42 is movable on the proximal end side relative to the constricted portion 38 of the pressing tube 18. The latch portion 42 has a first latch member 50A and a second latch member 50B. The first latch member 50A and the second latch member 50B extend parallelly from a proximal end part of the coupling member body 39 toward the proximal end side so as to face each other. The first latch member 50A and the second latch member 50B are disposed with a constant distance therebetween in the first direction.

Each of the first latch member 50A and the second latch member 50B has a top portion 52, an inclined portion 54, and an extension portion 56.

The two top portions 52 of the first latch member 50A and the second latch member 50B are disposed on the proximal end side from the coupling member body 39 and are formed so that end parts thereof on the distal end side are angular parts. The outside diameter of the two top portions 52 is larger than the outside diameter of the coupling member body 39, and is smaller than the inside diameter of the pressing tube 18. That is, the two top portions 52 have distal end surfaces whose end parts on the distal end parts are angular parts. In a state in which an external force is not applied to the two top portions 52, the inside diameter of the latch hole 36 in the proximal end surface of the pressing tube 18 is slightly smaller than the outside diameter of the two top portions 52 at the angular parts on the distal end side.

The two inclined portions 54 of the first latch member 50A and the second latch member 50B are disposed on the proximal end side from the two top portions 52, and the diameter thereof gradually decreases from the distal end side toward the proximal end side.

The two extension portions 56 of the first latch member 50A and the second latch member 50B are formed so as to extend further from the inclined portions 54 toward the proximal end side. That is, the two top portions 52, the two inclined portions 54, and the two extension portions 56 extend parallelly so as to face each other. The outside diameter of the two extension portions 56 is substantially the same as the outside diameter of most proximal end parts of the two inclined portions 54, and is slightly smaller than the inside diameter of the latch hole 36 in the proximal end surface of the pressing tube 18.

Figure 6:
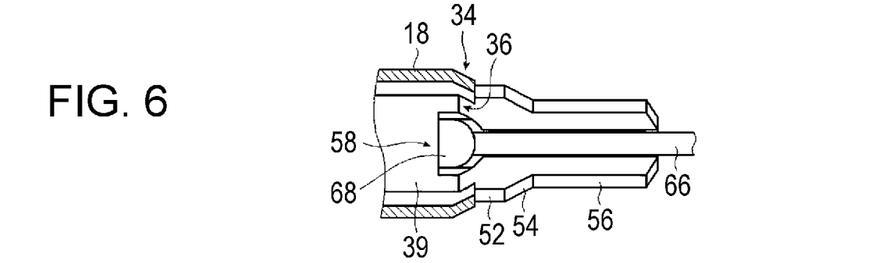
FIG. 6 is a partial sectional view of a proximal end side of the coupling member according to the embodiment.

FIG. 6 is a partial sectional view of the proximal end side of the coupling member according to the embodiment.

As illustrated in FIG. 6, the coupling member body 39 has a containing portion 58 formed therein. The containing portion 58 is a portion to which a distal end part of an operation wire 66 is removably latched. The containing portion 58 is formed in a part of the coupling member 20 on the distal end side relative to the two top portions 52 of the coupling member 20, that is, in the coupling member body 39. The containing portion 58 is a semicylindrical space, extends in the second direction at a position in the coupling member body 39 corresponding to a space between the first latch member 50A and the second latch member 50B of the coupling member 20, and is formed so that a curved surface thereof faces the proximal end side, that is, toward the space between the first latch member 50A and the second latch member 50B. An opening that is connected to the space between the first latch member 50A and the second latch member 50B is formed on the proximal end side of the containing portion 58. The size of the opening of the containing portion 58 in the first direction is substantially the same as the distance between the first latch member 50A and the second latch member 50B.

Figure 7:
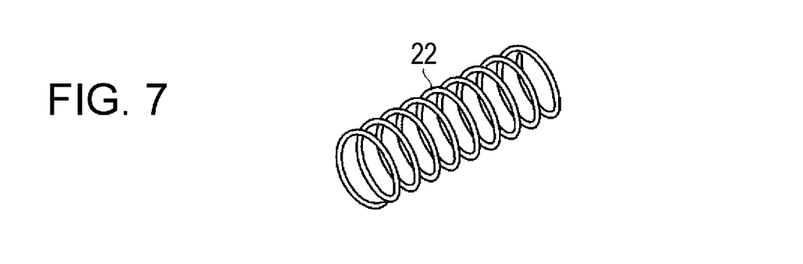
FIG. 7 is an external perspective view of an urging member according to the embodiment.

FIG. 7 is an external perspective view of an urging member according to the embodiment. The urging member 22 is contained in the pressing tube 18. In the present embodiment, the urging member 22 has a compression spring, as illustrated in FIG. 7. The urging member 22 is disposed so as to cover the outer surface of the coupling member body 39 of the coupling member 20, and is disposed between the two protruding portions 48 of the coupling member 20 and the constricted portion 38 of the pressing tube 18. That is, an end part of the urging member 22 on the distal end side is in contact with proximal end surfaces of the two protruding portions 48, and an end part of the urging member 22 on the proximal end side is in contact with an end surface of the constricted portion 38 of the pressing tube 18 on the distal end side.

In accordance with movement of the coupling member 20 relative to the pressing tube 18 from the distal end side toward the proximal end side, the urging member 22 is gradually compressed and elastically deforms. On the other hand, in accordance with movement of the coupling member 20 relative to the pressing tube 18 from the proximal end side toward the distal end side, the urging member 22 extends, urges the coupling member 20 relative to the pressing tube 18 from the proximal end side toward the distal end side by using an elastic force thereof, and moves the coupling member 20 and the clip body 16 relative to the pressing tube 18 from the proximal end side toward the distal end side.

The clip body 16, the pressing tube 18, and the urging member 22 of the clip unit 12 are made of a material such as a stainless steel, titanium, or a cobalt-chrome alloy. Accordingly, even after the clip unit 12 is placed in the body of a patient, the patient can have a magnetic resonance imaging (MM) scan.

The treatment tool body 14 includes an insertion portion 60 and an operation portion (not shown).

The insertion portion 60 includes a coil sheath 62, a tube sheath 64, and the operation wire 66.

The coil sheath 62 and the tube sheath 64 are flexible tubes that are made of, for example, a fluorocarbon resin such as polytetrafluoroethylene (PTFE) or a resin material such as high-density polyethylene (HDPE). The coil sheath 62 is inserted through the inside of the tube sheath 64. The inside diameter of a distal end part of the coil sheath 62 is slightly larger than the outside diameter of a proximal end part of the pressing tube 18. The proximal end part of the pressing tube 18 is fitted into the distal end part of the coil sheath 62, and the pressing tube 18 is removably attached to the coil sheath 62.

The operation wire 66 is made from, for example, a single wire or a stranded wire made of a metal. The operation wire 66 is inserted through the inside of the coil sheath 62 so as to be movable in the axial direction of the coil sheath 62.

The operation wire 66 moves in the coil sheath 62 toward the distal end side or the proximal end side. That is, the operator can push the operation wire 66 from the proximal end side toward the distal end side or pull the operation wire 66 from the distal end side toward the proximal end side.

Figure 8:
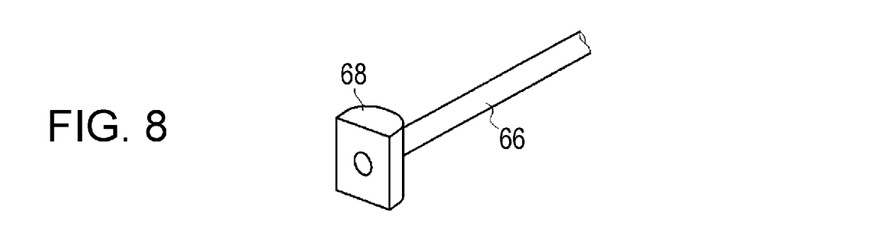
FIG. 8 is an external perspective view of a distal end side of an operation wire according to the embodiment.

FIG. 8 is an external perspective view of a distal end side of the operation wire according to the embodiment. As illustrated in FIG. 8, the operation wire 66 has a wire stopper 68 disposed on the distal end side thereof. The wire stopper 68 has a semicylindrical shape that is substantially the same as that of the containing portion 58 of the coupling member body 39. The outside diameter of the wire stopper 68 is slightly smaller than the inside diameter of the containing portion 58. The distal end side of the operation wire 66 is fixed to a middle part of a curved surface of the wire stopper 68 having a semicylindrical shape.

As illustrated in FIG. 6, the wire stopper 68 is contained in the containing portion 58. The diameter of the operation wire 66 is smaller than the distance between the first latch member 50A and the second latch member 50B of the coupling member 20, and the operation wire 66 is inserted through the space between the first latch member 50A and the second latch member 50B. Thus, the coupling member body 39 and the wire stopper 68 are latched to each other, and the coupling member 20 and the operation wire 66 are removably latched to each other.

As described above, the distal end part of the coupling member 20 is engaged with the folded portion 26 of the clip body 16, the coupling member 20 and the operation wire 66 are removably latched to each other, and the clip body 16 and the operation wire 66 are coupled by the coupling member 20.

The operation portion of the treatment tool body 14 has an operation portion body, a slider, and the like (not shown). A distal end part of the operation portion body is attached to a proximal end part of the coil sheath 62. The slider is a portion that moves the operation wire 66 relative to the coil sheath 62 toward the distal end side or the proximal end side. The slider is slidable relative to the operation portion body toward the distal end side or the proximal end side. A proximal end part of the operation wire 66 is fixed to a distal end part of the slider.

When an operator operates the operation portion of the clip treatment tool 10 and the slider is moved relative to the operation portion body toward the distal end side or the proximal end side, the operation wire 66 moves toward the distal end side or the proximal end side. In accordance with movement of the operation wire 66 from the proximal end side toward the distal end side, the coupling member 20 and the clip body 16 move from the proximal end side toward the distal end side. In accordance with movement of the operation wire 66 from the distal end side toward the proximal end side, the coupling member 20 and the clip body 16 move from the distal end side toward the proximal end side.

Next, actions of the clip treatment tool 10 will be described. First, an action that is performed when ligating a treatment part by using the clip unit 12 will be described. In the following description, it is assumed that an insertion portion of an endoscope (not shown) has already been inserted into the body of a patient.

First, when operated by an operator, the insertion portion 60 of the clip treatment tool 10 is inserted from a treatment tool inlet of the endoscope (not shown), and a distal end part of the insertion portion 60 of the clip treatment tool 10, to be more specific, a distal end part of the clip unit 12 is extruded from a treatment tool outlet of the endoscope.

Next, when the operator operates the operation portion of the clip treatment tool 10, the operation wire 66 is moved from the proximal end side toward the distal end side.

Figure 9B:
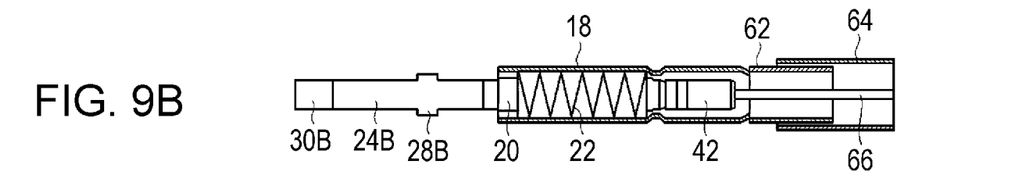
FIG. 9B is a partially see-through external side view of the clip treatment tool according to the embodiment illustrated in FIG. 9A, as seen in a different direction.

In accordance with movement of the operation wire 66 from the proximal end side toward the distal end side, the urging member 22 extends, and the coupling member 20 and the clip body 16 are urged by the urging member 22 and move from the proximal end side toward the distal end side. Thus, as illustrated in FIGS. 9A and 9B, the two arm portions 24A and 24B of the clip body 16 enter the open state.

Next, when operated by the operator, the insertion portion 60 is moved from the proximal end side toward the distal end side, and the distal end parts of the two arm portions 24A and 24B in the open state are pressed against a treatment part.

Next, in the state in which the distal end parts of the two arm portions 24A and 24B in the open state are pressed against the treatment part, when the operator operates the operation portion of the clip treatment tool 10, the operation wire 66 is moved from the distal end side toward the proximal end side.

In accordance with movement of the operation wire 66 from the distal end side toward the proximal end side, the urging member 22 is compressed. The coupling member 20 and the clip body 16 move from the distal end side toward the proximal end side against the urging force of the urging member 22, the two arm portions 24A and 24B are pressed by the distal end part of the pressing tube 18 in directions toward each other and elastically deform, and the two arm portions 24A and 24B gradually close from the open state.

In a state before the coupling member 20 is locked to the pressing tube 18, in accordance with movement of the coupling member 20 toward the distal end side or the proximal end side, the two arm portions 24A and 24B can be opened and closed.

In accordance with movement of the coupling member 20 from the distal end side toward the proximal end side, the urging member 22 is compressed. The clip body 16 moves from the distal end side toward the proximal end side, the two arm portions 24A and 24B are pressed by the distal end part of the pressing tube 18 in directions toward each other and elastically deform, and the two arm portions 24A and 24B gradually close from the open state (fully open state) and finally enter the closed state (fully closed state). In accordance with movement of the coupling member 20 from the distal end side toward the proximal end side, the latch portion 42 of the coupling member 20 moves from the distal end side toward the proximal end side, passes through the latch hole 36 of the pressing tube 18, and protrudes from the proximal end surface of the pressing tube 18.

On the other hand, in accordance with movement of the coupling member 20 from the proximal end side toward the distal end side, the urging member 22 extends, and the coupling member 20 is urged by the urging member 22 and moves further from the proximal end side toward the distal end side. The clip body 16 moves from the proximal end side toward the distal end side, and the two arm portions 24A and 24B gradually open from the closed state due to an elastic force and finally enter the open state. In accordance with movement of the coupling member 20 from the proximal end side toward the distal end side, the latch portion 42 of the coupling member 20 moves from the proximal end side toward the distal end side, passes through the latch hole 36 of the pressing tube 18, and becomes contained in the pressing tube 18.

Thus, in the state before the coupling member 20 is locked to the pressing tube 18, it is possible to hold a treatment part over again by using the first claw portion 30A and the second claw portion 30B of the two arm portions 24A and 24B by opening and closing the two arm portions 24A and 24B. Therefore, it is possible to hold a target treatment part accurately.

Next, in the state in which the treatment part is held by the first claw portion 30A and the second claw portion 30B of the two arm portions 24A and 24B, the operation wire 66 is moved further from the distal end side toward the proximal end side.

Accordingly, the urging member 22 is further compressed, the coupling member 20 and the clip body 16 move further from the proximal end side toward the distal end side against an urging force of the urging member 22, and the two arm portions 24A and 24B further close.

In accordance with further movement of the coupling member 20 from the distal end side toward the proximal end side, the latch portion 42 of the coupling member 20 move furthers from the distal end side toward the proximal end side, and the extension portion 56 of the latch portion 42 passes through the latch hole 36 of the pressing tube 18 and protrudes from the proximal end surface of the pressing tube 18.

In accordance with further movement of the latch portion 42 from the distal end side toward the proximal end side, the two inclined portions 54 of the coupling member 20 are pressed by a distal end part of the latch hole 36 in directions toward each other, and the first engagement member 44A and the second engagement member 44B of the latch portion 42 are bent in directions toward each other. Thus, the two inclined portions 54, the two top portions 52, and the two extension portions 56 are reduced in diameter and pass through the latch hole 36.

When the latch portion 42 moves toward the distal end side or the proximal end side, inclined surfaces (outer surfaces) of the two inclined portions 54 and an inner peripheral surface of the distal end part of the latch hole 36 of the pressing tube 18 contact each other, and the inclined surfaces of the two inclined portions 54 slide along the inner peripheral surface of the distal end part of the latch hole 36. When the latch portion 42 slides along the inner peripheral surface of the distal end part of the latch hole 36, the inclined surfaces of the two inclined portions 54 function to reduce friction between the latch portion 42 and the latch hole 36, and to facilitate movement of the latch portion 42 relative to the latch hole 36 toward the distal end side or the proximal end side.

In accordance with further movement of the latch portion 42 from the distal end side toward the proximal end side, the angular parts at the distal end side of the two top portions 52 move to positions beyond the latch hole 36, and the two top portions 52, which have been reduced in diameter, move away from each other due to an elastic force. Thus, the outside diameter of the two top portions 52 at the angular parts on the distal end side becomes larger than the inside diameter of the latch hole 36, and the angular parts on the distal end side of the two top portions 52 are latched to the proximal end surface of the latched portion 34. That is, the latch portion 42 is latched to the latched portion 34.

Figure 10A:
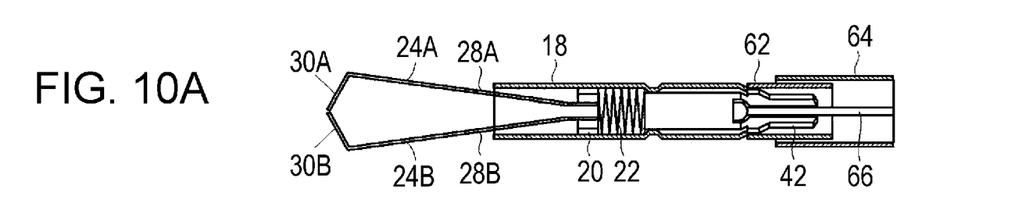
FIG. 10A is a partially see-through external side view of the clip treatment tool according to the embodiment of the present invention, in a state in which two arm portions of the clip body are in a closed state.
Figure 10B:
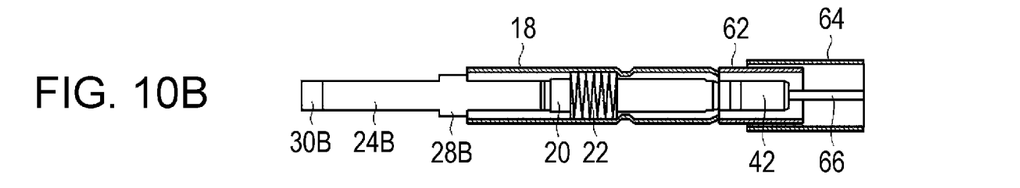
FIG. 10B is a partially see-through external side view of the clip treatment tool according to the embodiment illustrated in FIG. 10A, as seen in a different direction.

When the angular parts on the distal end side of the two top portions 52 move to positions beyond the latch hole 36, the two arm portions 24A and 24B enter the closed state as illustrated in FIGS. 10A and 10B.

Thus, the coupling member 20 is locked to the pressing tube 18 while the two arm portions 24A and 24B are in the closed state, and a treatment part is ligated by the first claw portion 30A and the second claw portion 30B of the two arm portions 24A and 24B.

Next, in the state in which the coupling member 20 is locked to the pressing tube 18, that is, in the state in which the treatment part is ligated by the first claw portion 30A and the second claw portion 30B of the two arm portions 24A and 24B, the operation wire 66 is moved further from the distal end side toward the proximal end side.

Accordingly, the coupling member 20 and the clip body 16 move further from the distal end side toward the proximal end side, and end parts of the first protruding portion 28A and the second protruding portion 28B of the two arm portions 24A and 24B on the proximal end side contact the distal end part of the pressing tube 18. Thus, movement of the coupling member 20 and the clip body 16 from the distal end side toward the proximal end side is restricted.

Next, in the state in which the coupling member 20 is locked to the pressing tube 18 and movement of the coupling member 20 and the clip body 16 from the distal end side toward the proximal end side is restricted, the operation wire 66 is moved further from the distal end side toward the proximal end side.

In accordance with movement of the operation wire 66 from the distal end side toward the proximal end side, the two top portions 52 of the coupling member 20 are pushed and expanded by an end part of the wire stopper 68 on the proximal end side, that is, the curved surface in the first direction, and move away from each other, and the wire stopper 68 is removed from the containing portion 58 of the coupling member 20. Thus, the coupling member 20 and the operation wire 66 are separated from each other.

Next, in the state in which the coupling member 20 and the operation wire 66 are separated from each other, the operation wire 66 is moved from the proximal end side toward the distal end side.

In accordance with movement of the operation wire 66 from the proximal end side toward the distal end side, the wire stopper 68 moves from the proximal end side toward the distal end side, and the distal end part of the wire stopper 68 contacts a proximal end part of the latch portion 42 of the coupling member 20.

Figure 11A:
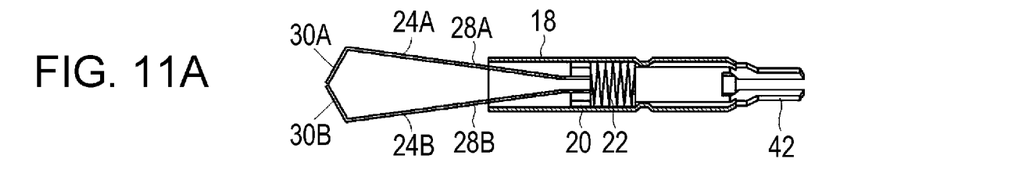
FIG. 11A is a partially see-through external side view of a clip unit according to the embodiment in a state in which the clip unit is separated from the coil sheath.
Figure 11B:
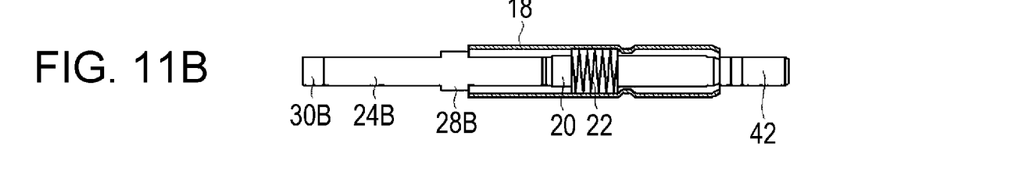
FIG. 11B is a partially see-through external side view of the clip unit according to the embodiment illustrated in FIG. 11A, as seen in a different direction.

In accordance with further movement of the operation wire 66 from the proximal end side toward the distal end side, the wire stopper 68 pushes the latch portion 42 of the coupling member 20, that is, the clip body 16 toward the distal end side, and the clip unit 12 is separated from the coil sheath 62 as illustrated in FIGS. 11A and 11B. Thus, in the state in which the clip unit 12 ligates the treatment part, the clip unit 12 is placed at the treatment part.

Subsequently, when operated by the operator, in the state in which the insertion portion 60 of the clip treatment tool 10 is still inserted into the endoscope, the insertion portion of the endoscope is pulled out from the inside of the body of the patient. To ligate a plurality of treatment parts, the action described above is repeatedly performed.

Next, actions that are performed to remove the clip unit 12 from a treatment part will be described. First, an action that is performed to remove the clip unit 12 by using a grasping member, such as grasping forceps, whose grasping portion opens and closes when an operator operates the operation portion, will be described.

Figure 12:
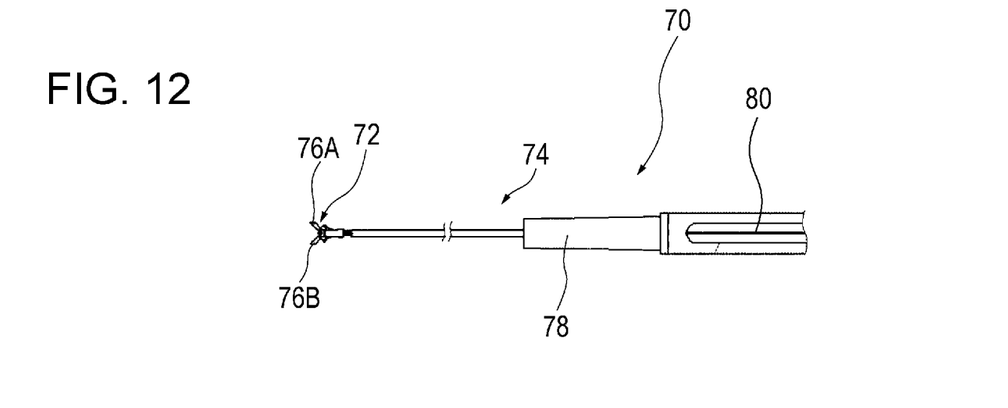
FIG. 12 is a side view illustrating a distal end portion of grasping forceps according to an embodiment.

FIG. 12 is a side view of a distal end portion of grasping forceps according to an embodiment. Grasping forceps 70 illustrated in FIG. 12 include a grasping portion 72, an insertion portion 74, and an operation portion (not shown). The grasping portion 72 is attached to a distal end part of the insertion portion 74, and the operation portion (not shown) is attached to a proximal end part of the insertion portion 74.

The grasping portion 72 has a pair of claw members 76A and 76B. The claw members 76A and 76B open and close when the operator operates the operation portion. The claw members 76A and 76B extend from the proximal end side toward the distal end side, and are disposed so as to face each other when grasping surfaces thereof are in a closed state.

The insertion portion 74 includes a sheath 78 and an operation wire 80. The operation wire 80 is inserted through the inside of the sheath 78 so as to be movable back and forth. The grasping portion 72 is attached to a distal end part of the sheath 78, and a distal end part of the operation wire 80 is fixed to proximal end parts of the claw members 76A and 76B of the grasping portion 72.

When the operator operates the operation portion, the operation wire 80 moves from the distal end side toward the proximal end side, and the pair of claw members 76A and 76B gradually close from an open state (an ungrasping state) and finally enter a closed state (a grasping state). On the other hand, when the operation wire 80 moves from the proximal end side toward the distal end side, the pair of claw members 76A and 76B gradually open from the close state and finally enter the open state.

To remove the clip unit 12, first, when operated by the operator, the insertion portion 74 of the grasping forceps 70 is inserted from a treatment tool inlet of an endoscope (not shown), and the distal end part of the insertion portion 74 of the grasping forceps 70, to be more specific, the grasping portion 72 at the distal end part of the grasping forceps 70 is extruded from the treatment tool outlet of the endoscope.

Figure 13:
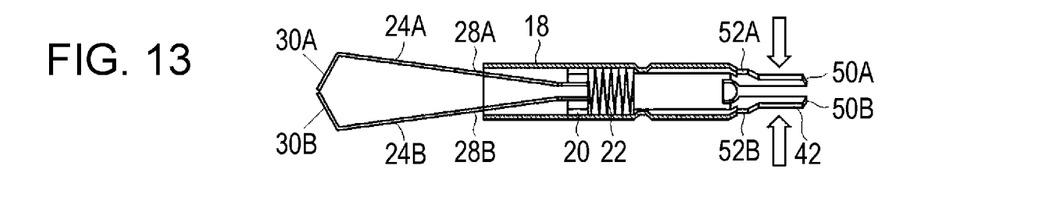
FIG. 13 is an external sectional view of the clip unit according to the embodiment, in a state in which a latch portion of the coupling member, which is locked to the pressing tube, is pressed from both outer sides.

Next, in the state in which the coupling member 20 and the operation wire 66 are separated from each other, that is, in the state in which the clip unit 12 is placed at the treatment part, when the operator operates the operation portion of the grasping forceps 70, the claw members 76A and 76B of the grasping portion 72 of the grasping forceps 70 are caused to enter the open state. Next, the claw members 76A and 76B of the grasping portion 72 in the open state are gradually closed, and, as indicated by arrows in FIG. 13, the first latch member 50A and the second latch member 50B of the latch portion 42 of the coupling member 20 are clamped by the claw members 76A and 76B of the grasping forceps 70 from both outer sides in the first direction, that is, in the direction in which the first latch member 50A and the second latch member 50B face each other. Thus, the two top portions 52 of the coupling member 20 are pressed from both outer sides.

Figure 14:
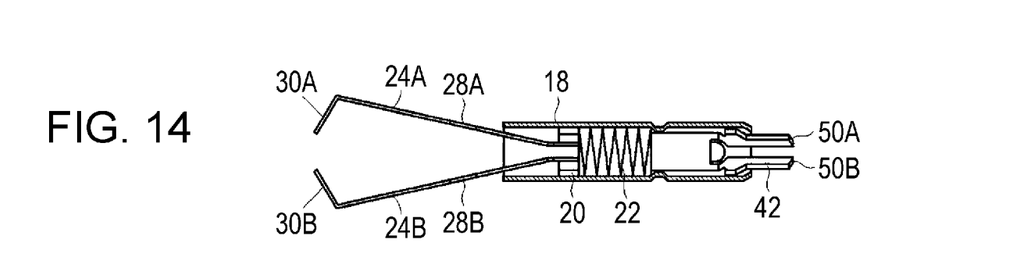
FIG. 14 is an external sectional view of the clip unit according to the embodiment, in a state in which the coupling member and pressing tube are unlocked and the coupling member and the clip body have moved toward the distal end side.
Figure 15:
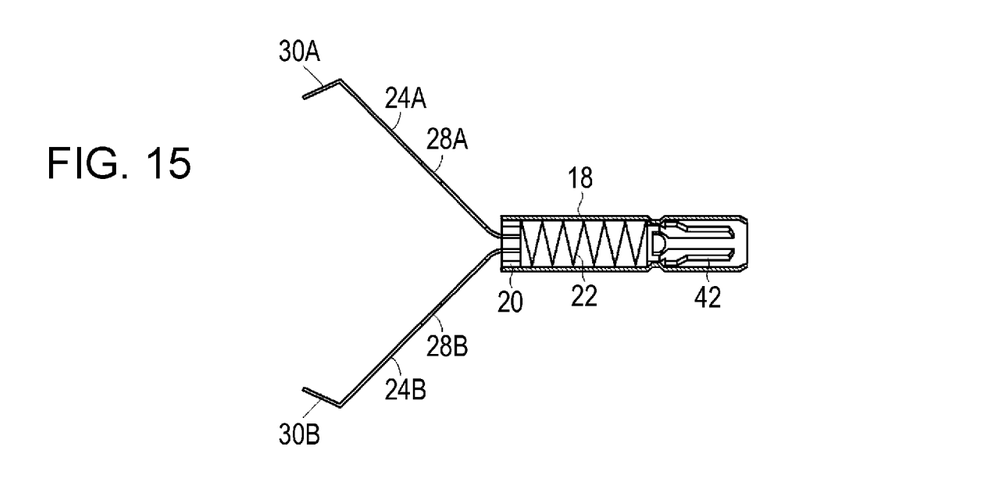
FIG. 15 is a sectional view of the clip unit according to the embodiment illustrated in FIG. 14, in a state in which the coupling member and the clip body have moved further toward the distal end side and the two arm portions of the clip body are opened.

When the two top portions 52 are pressed from both outer sides and move closer to each other, the outside diameter of the two top portions 52 at the angular parts on the distal end side becomes smaller than the inside diameter of the latch hole 36, and the coupling member 20 and the pressing tube 18 are unlocked. When the coupling member 20 and the pressing tube 18 are unlocked, as illustrated in FIG. 14, the coupling member 20 is urged by the urging member 22 and moves from the proximal end side toward the distal end side. In accordance with movement of the coupling member 20 from the proximal end side toward the distal end side, as illustrated in FIG. 15, the clip body 16 moves from the proximal end side toward the distal end side, and the two arm portions 24A and 24B gradually open from the closed state due to an elastic force and finally return to the open state. Thus, the clip unit 12 is removed from the treatment part.

Subsequently, when operated by the operator, in the state in which the insertion portion 74 of the grasping forceps 70 is still inserted into the endoscope, the insertion portion of the endoscope is pulled out from the inside of the body of the patient. For example, in the state in which an appropriate part of the clip unit 12 is clamped by the claw members 76A and 76B of the grasping portion 72 of the grasping forceps 70, the insertion portion of the endoscope is pulled out from the inside of the body of the patient, and the clip unit 12, which has been removed from the treatment part, is also taken to the outside of the body of the patient at the same time. To remove a plurality of clip units 12, the action described above is repeatedly performed.

Next, an action that is performed to remove the clip unit 12 by using a snare member, whose loop diameter increases and decreases when an operator operates an operation portion, will be described.

Figure 16:
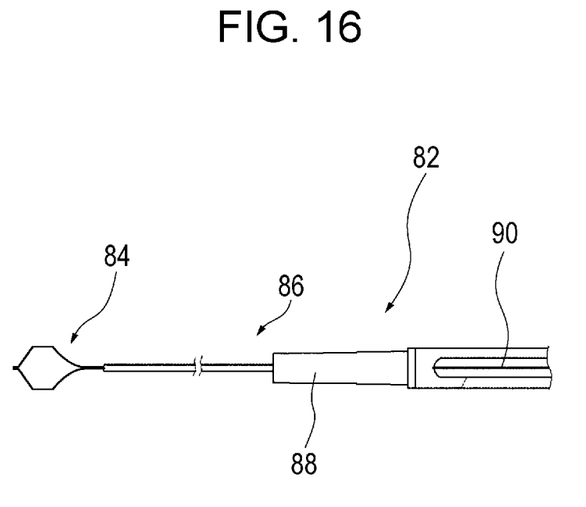
FIG. 16 is a side view illustrating a distal end portion of a snare member according to an embodiment.

FIG. 16 is a side view of a distal end portion of a snare member according to an embodiment. A snare member 82 illustrated in FIG. 16 includes a loop portion 84, an insertion portion 86, and the operation portion (not shown). The loop portion 84 is attached to a distal end part of an operation wire 90 inserted through the inside of the insertion portion 86 described below, and the operation portion (not shown) is attached to a proximal end part of the insertion portion 86.

The loop portion 84 is formed by bending a wire. The bent portion of the wire is oriented toward the distal end side. When the operator operates the operation portion, the loop diameter of the loop portion 84 decreases.

The insertion portion 86 includes a sheath 88 and the operation wire 90. The operation wire 90 is inserted through the inside of the sheath so as to be movable back and forth. Both end parts of the wire of the loop portion 84 are attached to a distal end part of the sheath 88 and are fixed to the distal end part of the operation wire 90.

When the operator operates the operation portion and the operation wire 90 moves from the distal end side toward the proximal end side, the loop portion 84 is inserted into the sheath 88 and the loop diameter of the loop portion 84 decreases. On the other hand, when the operation wire 90 moves from the proximal end side toward the distal end side, the loop portion 84 is extruded from the distal end part of the sheath 88, and the diameter of the loop portion 84 increases.

To remove the clip unit 12, first, when operated by the operator, the insertion portion 86 of the snare member 82 is inserted from a treatment tool inlet of an endoscope (not shown), and a distal end part of the insertion portion 86 of the snare member 82, to be more specific, the loop portion 84 at the distal end part of the snare member 82 is extruded from a treatment tool outlet of the endoscope.

Next, in the state in which the coupling member 20 and the operation wire 66 are separated from each other, that is, in the state in which the clip unit 12 is placed at a treatment part, when the operator operates the operation portion of the snare member 82, the loop diameter of the loop portion 84 of the snare member 82 is increased. Next, the loop diameter of the loop portion 84, which has been increased, gradually decreases, as indicated by arrows in FIG. 13, the first latch member 50A and the second latch member 50B of the latch portion 42 of the coupling member 20 are fastened by the loop portion 84 and are pressed from both outer sides in the first direction, that is, the direction in which the first latch member 50A and the second latch member 50B face each other. Thus, the two top portions 52 of the coupling member 20 are pressed from both outer sides.

When the two top portions 52 are pressed from both outer sides and move closer to each other, the outside diameter of the two top portions 52 at the angular parts on the distal end side becomes smaller than the inside diameter of the latch hole 36, and the coupling member 20 and the pressing tube 18 are unlocked. When the coupling member 20 and the pressing tube 18 are unlocked, as illustrated in FIG. 14, the coupling member 20 is urged by the urging member 22 and moves from the proximal end side toward the distal end side. In accordance with movement of the coupling member 20 from the proximal end side toward the distal end side, as illustrated in FIG. 15, the clip body 16 moves from the proximal end side toward the distal end side, and the two arm portions 24A and 24B gradually open from the closed state due to an elastic force and finally return to the open state. Thus, the clip unit 12 is removed from the treatment part.

Subsequently, when operated by the operator, in the state in which the insertion portion 86 of the snare member 82 is still inserted into the endoscope, the insertion portion of the endoscope is pulled out from the inside of the body of the patient. For example, in the state in which an appropriate part of the clip unit 12 is fastened by the loop portion 84 of the snare member 82, the insertion portion of the endoscope is pulled out from the inside of the body of the patient, and the clip unit 12, which has been removed from the treatment part, is also taken to the outside of the body of the patient at the same time. To remove a plurality of clip units 12, the action described above is repeatedly performed.

With the clip treatment tool 10, until a treatment part is ligated by the clip unit 12, it is possible to hold the treatment part over again by using the two arm portions 24A and 24B, and, after the treatment part has been ligated by the clip unit 12, because the coupling member 20 and the pressing tube 18 are locked, it is possible to reliably maintain the state in which the treatment part is ligated by the clip unit 12. Moreover, after the clip unit 12 is placed at the treatment part, it is possible to remove the clip unit 12 from the treatment part by unlocking the coupling member 20 and the pressing tube 18 at any desirable timing.

The first protruding portion 28A and the second protruding portion 28B of the clip body 16 are not essential elements. Even if the first protruding portion 28A and the second protruding portion 28B are omitted, movement of the clip body 16 from the distal end side toward the proximal end side is restricted to a position where the urging member 22 is maximally compressed.

The shape of the folded portion 26 of the clip body 16 and the shapes of the engagement holes 32A and 32B and the first projecting portion 46A and the second projecting portion of the coupling member 20 may be any shapes, as long as it is possible to engage the folded portion 26 with the engagement portion 40 of the coupling member 20.

In the embodiment described above, the proximal end surface of the latched portion 34 of the pressing tube 18 is formed as an inclined surface by reducing the diameter of the proximal end side of the pressing tube 18. However, this is not a limitation, and the proximal end surface may extend from the inner peripheral surface on the proximal end side of the pressing tube 18 toward the central axis.

In the embodiment described above, the protruding portions 48 of the coupling member 20 are respectively formed on the outer surfaces of the first engagement member 44A and the second engagement member 44B on the distal end side. However, this is not a limitation, and the coupling member 20 may have a proximal end surface that contacts the end part of the urging member 22 on the distal end side. For example, a protruding portion 48 may be formed on the outer surface of one of the first engagement member 44A and the second engagement member 44B on the distal end side, or may be disposed on the outer surface of the coupling member body 39 on the distal end side.

The shapes of the containing portion 58 of the coupling member 20 and the wire stopper 68 may be any shapes, as long as it is possible to latch the coupling member 20 and the operation wire 66 to each other by latching the coupling member body 39 and the wire stopper 68 to each other and to remove the wire stopper 68 from the containing portion 58.

When removing the clip unit 12, the first latch member 50A and the second latch member 50B of the latch portion 42 of the coupling member 20 are pressed from both outer sides and the two top portions 52 are pressed from both outer sides. However, for example, the two top portions 52 may be pressed from both outer sides by pressing the two extension portions 56 or the two inclined portions 54 from both outer sides, or the two top portions 52 may be directly pressed from both outer sides.

Heretofore, the present invention has been described in detail. The present invention is not limited to the embodiment described above, and naturally, various improvements and modifications are possible within the spirit and scope of the present invention.

REFERENCE SIGNS LIST

10 clip treatment tool
12 clip unit
14 treatment tool body
16 clip body
18 pressing tube
20 coupling member
22 urging member
24A first arm portion
24B second arm portion
26 folded portion
28A first protruding portion
28B second protruding portion
30A first claw portion
30B second claw portion
32A, 32B engagement hole
34 latched portion
36 latch hole
38 constricted portion
39 coupling member body
40 engagement portion
42 latch portion
44A first engagement member
44B second engagement member
46A first projecting portion
48 protruding portion
50A first latch member
50B second latch member
52 top portion
54 inclined portion
56 extending portion
58 containing portion
60, 74, 86 insertion portion
62 coil sheath
64 tube sheath
66, 80, 90 operation wire
68 wire stopper
70 grasping forceps
72 grasping portion
76A, 76B claw member
78, 88 sheath
82 snare member
84 loop portion

What is claimed is:

1. A clip treatment tool comprising:
   a clip body that has two arm portions that face each other and open and close and a folded portion that connects proximal end parts of the two arm portions;
   a pressing tube that opens the two arm portions and exposes the clip body in accordance with movement of the clip body from a proximal end side toward a distal end side and that closes the two arm portions and allows the clip body to be contained therein in accordance with movement of the clip body from the distal end side toward the proximal end side;

a coupling member that has a distal end part engaged with the folded portion of the clip body and a proximal end part to which a distal end part of an operation wire is removably latched, the coupling member coupling the clip body and the operation wire to each other; and an urging member that is contained in the pressing tube and that urges the coupling member relative to the pressing tube from the proximal end side toward the distal end side, wherein the pressing tube has a latched portion disposed on the proximal end side of the pressing tube, and the coupling member has a latch portion disposed on the proximal end side of the coupling member, and wherein, in accordance with movement of the operation wire from the distal end side toward the proximal end side, the coupling member moves from the distal end side toward the proximal end side, the latch portion is latched to the latched portion, and the coupling member is locked to the pressing tube.

2. The clip treatment tool according to claim 1,
wherein, in accordance with movement of the coupling member from the distal end side toward the proximal end side, the two arm portions are pressed by a distal end part of the pressing tube in directions toward each other and elastically deform, and the two arm portions gradually close from an open state and enter a closed state.

3. The clip treatment tool according to claim 2,
wherein the pressing tube has a constricted portion in a middle part thereof in an axial direction, the constricted portion having an inside diameter smaller than an inside diameter at both end parts of the pressing tube, and the coupling member has a protruding portion on the distal end side, the protruding portion having an outside diameter that is larger than an outside diameter at a middle part of the coupling member, and wherein the urging member is disposed between the protruding portion and the constricted portion, and the latch portion is movable on the proximal end side relative to the constricted portion.

4. The clip treatment tool according to claim 2,
wherein the latch portion has two top portions that are formed so that end parts thereof on the distal end side are angular parts and two inclined portions that are respectively disposed on the proximal end side from the two top portions, and the two top portions and the two inclined portions extend so as to face each other, wherein the latched portion has a proximal end surface formed on the proximal end side of the pressing tube, and a latch hole is formed in the proximal end surface of the pressing tube, the latch hole having an inside diameter that is smaller than an outside diameter of the two top portions at the angular parts on the distal end side, and wherein, in accordance with movement of the coupling member from the distal end side toward the proximal end side, the two inclined portions are pressed by a distal end part of the latch hole in directions toward each other and pass through the latch hole, the angular parts of the two top portions move to positions beyond the latch hole of the latched portion, the two top portions move away from each other due to an elastic force and the angular parts of the two top portions are latched to the proximal end surface of the latched portion, and the coupling member is locked to the pressing tube while the two arm portions are in the closed state.

5. The clip treatment tool according to claim 4,
wherein the pressing tube has a constricted portion in a middle part thereof in an axial direction, the constricted portion having an inside diameter smaller than an inside diameter at both end parts of the pressing tube, and the coupling member has a protruding portion on the distal end side, the protruding portion having an outside diameter that is larger than an outside diameter at a middle part of the coupling member, and wherein the urging member is disposed between the protruding portion and the constricted portion, and the latch portion is movable on the proximal end side relative to the constricted portion.

6. The clip treatment tool according to claim 4,
wherein the coupling member has a containing portion that is formed in the coupling member on the distal end side relative to the two top portions, and the operation wire has a wire stopper that is disposed on the distal end side of the operation wire and that is contained in the containing portion, and wherein, in a state in which the coupling member is locked to the pressing tube, in accordance with movement of the operation wire from the distal end side toward the proximal end side, the two top portions are pushed and expanded by an end part of the wire stopper on the proximal end side and move away from each other, the wire stopper is removed from the containing portion, and the coupling member and the operation wire are separated from each other.

7. The clip treatment tool according to claim 6,
wherein the pressing tube has a constricted portion in a middle part thereof in an axial direction, the constricted portion having an inside diameter smaller than an inside diameter at both end parts of the pressing tube, and the coupling member has a protruding portion on the distal end side, the protruding portion having an outside diameter that is larger than an outside diameter at a middle part of the coupling member, and wherein the urging member is disposed between the protruding portion and the constricted portion, and the latch portion is movable on the proximal end side relative to the constricted portion.

8. The clip treatment tool according to claim 6,
wherein, in a state in which the coupling member and the operation wire are separated from each other, the two top portions are pressed from both outer sides, the outside diameter of the two top portions at the angular parts on the distal end side becomes smaller than the inside diameter of the latch hole, the coupling member is urged by the urging member and moves from the proximal end side toward the distal end side, and, in accordance with movement of the coupling member from the proximal end side toward the distal end side, the clip body moves from the proximal end side toward the distal end side, and the two arm portions gradually open from the closed state and return to the open state.

9. The clip treatment tool according to claim 8,
wherein the pressing tube has a constricted portion in a middle part thereof in an axial direction, the constricted portion having an inside diameter smaller than an inside diameter at both end parts of the pressing tube, and the coupling member has a protruding portion on the distal end side, the protruding portion having an outside diameter that is larger than an outside diameter at a middle part of the coupling member, and wherein the urging member is disposed between the protruding portion and the constricted portion, and the latch portion is movable on the proximal end side relative to the constricted portion.

10. The clip treatment tool according to claim 1, wherein the pressing tube has a constricted portion in a middle part thereof in an axial direction, the constricted portion having an inside diameter smaller than an inside diameter at both end parts of the pressing tube, and the coupling member has a protruding portion on the distal end side, the protruding portion having an outside diameter that is larger than an outside diameter at a middle part of the coupling member, and wherein the urging member is disposed between the protruding portion and the constricted portion, and the latch portion is movable on the proximal end side relative to the constricted portion.

\* \* \* \* \*